United States Patent [19]

Neckers

[11] Patent Number: 4,831,188

[45] Date of Patent: * May 16, 1989

[54] PERESTER PHOTOINITIATORS

[75] Inventor: Douglas C. Neckers, Perrysburg, Ohio

[73] Assignee: Bowling Green State University, Bowling Green, Ohio

[*] Notice: The portion of the term of this patent subsequent to Nov. 22, 2000 has been disclaimed.

[21] Appl. No.: 4,912

[22] Filed: Jan. 20, 1987

Related U.S. Application Data

[63] Continuation of Ser. No. 584,645, Feb. 29, 1984.

[51] Int. Cl.$^4$ ............................................. C07C 179/18
[52] U.S. Cl. .................................................... 560/302
[58] Field of Search ......................................... 560/302

[56] References Cited

U.S. PATENT DOCUMENTS 4,416,826 11/1983 Neckers ........................ 260/453 RZ

OTHER PUBLICATIONS

Abu-Abdoun et al., *J. Poly. Sci.: Polymer Chemistry Ed.*, vol. 21, pp. 3129–3144, Nov. 1983.
Thijs et al., *J. Org. Chem.*, vol. 44, No. 23, pp. 4123–4128, 1979.

*Primary Examiner*—Bruce D. Gray
*Attorney, Agent, or Firm*—Emch, Schaffer, Schaub & Porcello Co.

[57] ABSTRACT

Peresters of the formula: $R_1$ Ar COOOR wherein R is an alkyl group; Ar is selected from the group including phenyl (unsubstituted or substituted) groups, naphthyl groups, anthryl groups, pyryl groups, phenanthryl groups, or heterocyclic groups; and $R_1$ is any group absorbing radiation between 250 and 800 nm such that $R_1$ produces an excited state of sufficient lifetime to cause the decomposition to free radicals of the appended perester or peroxidic function.

14 Claims, 12 Drawing Sheets

PERESTER PHOTOINITIATORS

This application is a continuation of Ser. No. 584,645 filed Feb. 29, 1984.

BACKGROUND OF THE INVENTION

1. Technical Field

The present invention is based upon work supported by the National Science Foundation under NSF Grant DMR 81-03100.

The present invention is concerned with new organic compounds which are particularly suitable as photoinitiators. The present invention is especially concerned with peresters. The peresters of the present invention are especially useful as photoinitiators for the polymerization of ethylenically unsaturated materials.

2. Background Art

Photoinitiators are free-radical sources which decompose photochemically and are employed especially as initiators in the polymerization of ethylenically unsaturated materials. In view of the efficient control photoinitiated polymerization offers, such as assumed great importance in recent years in the printing and electronics industries such as in printing inks, paints and photoresist coatings.

Among typical commercial initiators are three general types: mixtures of aryl ketones, benzoin ethers, or substituted acetophenones. In past years, highly halogenated aryl hydrocarbons were also used for initiators, but their use is now precluded because they are so highly toxic.

Among the more important commercially used photoinitiators for acrylate polymerization is the so-called "Hammond initiator", benzophenone-Michler's ketone.

A major advantage of the Hammond initiator is the rate by which it initiates radical chain reactions; two important disadvantages are the rather large amount of initiator needed to make the rate of polymerization sufficiently rapid for printing applications and the potential toxicity of one of the initiator partners—Michler's ketone (4,4'-bis(N,N-dimethylamino)benzophenone).

To be of real practical significance as a photoinitiator, a compound must be relatively thermally stable but must also be labile when irradiated with wavelengths of UV or visible light. Accordingly, providing new compounds which possess this combination of properties is quite difficult. For instance, various benzophenone derivatives of benzoyl peroxide have been studied. For example, see Leffler et al; Journal American Chemical Society, 1971, 93, 7005 et seq. However, such derivatives are not especially stable thermally. It has also been noted that the photochemical efficiency of triplet benzophenone sensitized decompositions of peroxides in solution is low (e.g.—see Walling et al., Journal Americal Chemical Society, 1965, 87, 3413 et seq.).

SUMMARY OF INVENTION

An object of the present invention is to provide new compounds which have the requisite combination of relative thermal stability and efficient photodecomposability to be effective and practical photoinitiators.

The compounds of the present invention are peresters which contain a light absorbing chromophoric moiety. The compounds of the present invention exhibit thermal stability characteristics. However, the compounds of the present invention, unlike prior known peresters, are readily photodecomposable and effective photoinitiators for the polymerization of ethylenically unsaturated compounds. The present invention also makes it possible to control or tune the photodecomposition of the compounds by the absorption characteristics of the light-absorbing chromophore portion of the compound.

The compounds of the present invention are represented by the formula:

where Ar is selected from the group including phenyl (unsubstituted or substituted) groups; naphthyl groups; anthryl groups, pyryl groups, phenanthryl groups, heteroaromatic groups, and heterocyclic groups, including furan, thiophene, benzothiophene, benzothiazole, etc; Y is selected from the groups including $CH_2$, $C=O$, $C=N$; R is an alkyl group, and $R_1$ is any group absorbing radiation between 250 and 800 nm and $R_1$ is an organic group such that the group $R_1$ produces an excited state of sufficient lifetime to cause the decomposition to free radicals of the appended perester or peroxidic function.

The present invention is also concerned with photopolymerizable compositions comprising at least one photopolymerizable ethylenically unsaturated material and at least one of the above-discussed peresters.

Moreover, the present invention is concerned with polymerizing the above-defined photopolymerizable compositions by subjecting such to light, and polymer obtained thereby.

DESCRIPTION OF BEST AND VARIOUS MODES

Figure 1:
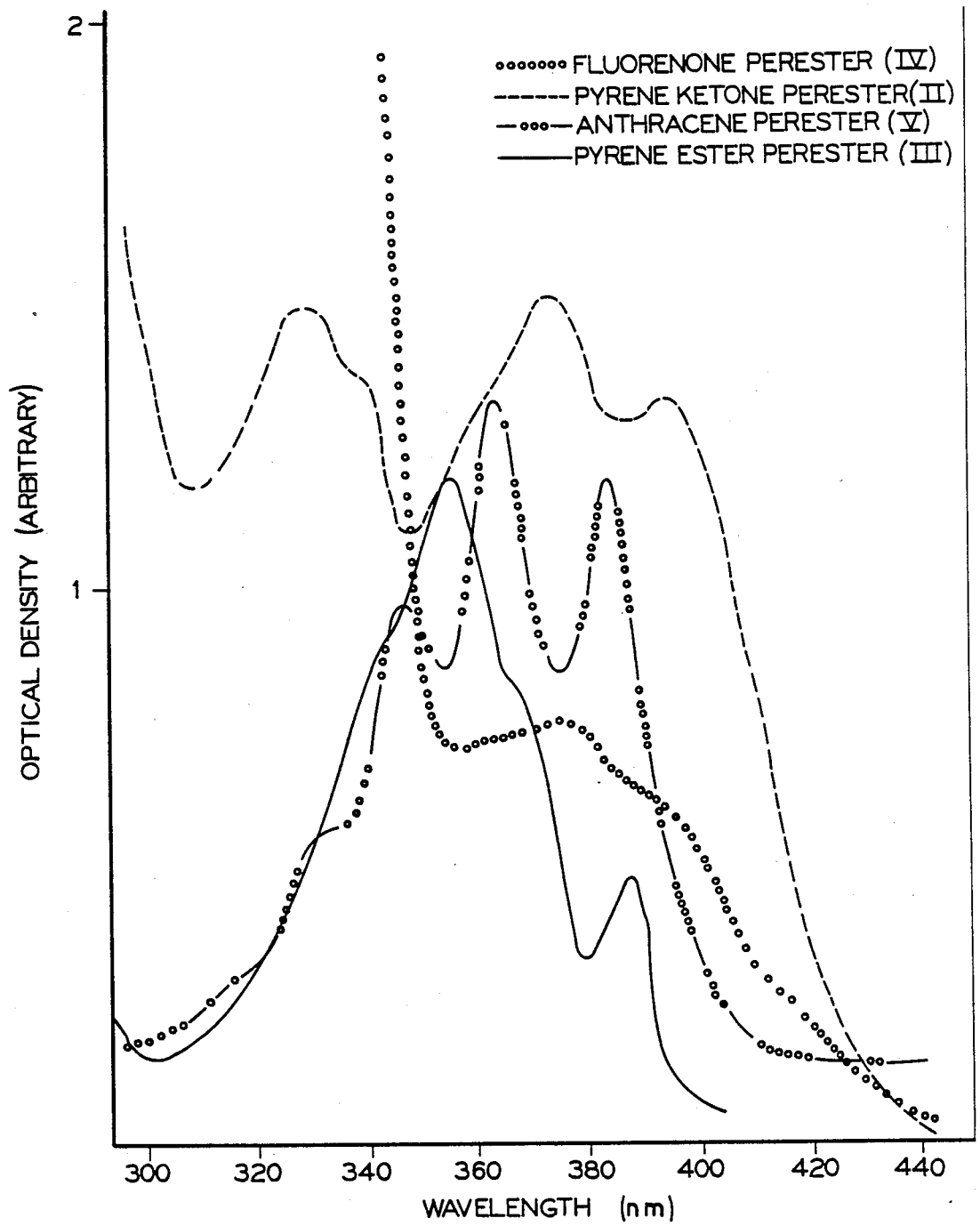
FIG. 1 is a graph showing UV spectra in dichloromethane.

The compounds of the present invention are represented by the formula:

$$R_1Y-ArCOOOR$$

where Ar is selected from the group including phenyl (unsubstituted or substituted) groups; naphthyl groups; anthryl groups, pyryl groups, phenanthryl groups, heteroaromatic groups or heterocyclic groups, including furan, thiophene, benzothiophene, benzothiazole, etc; Y is selected from the group including $CH_2$, $C=O$, $C=N$ etc., R is a $C_1-C_{22}$ alkyl group, and in a preferred embodiment R is a tertiary alkyl group, an alkyl group, and $R_1$ is any group absorbing radiation between 250 and 800 nm and $R_1$ is an organic group such that the group $R_1$ produces an excited state of sufficient lifetime to cause the decomposition to free radicals of the appended perester or peroxidic function.

Examples of some suitable $R_1$ groups are aryl groups, heteroaryl groups, polycyclic aryl groups, aralkyl groups, and substituted examples of all of these. Examples also include those containing heteroatoms such as oxygen, sulfur, nitrogen, phosphorous, etc.

Examples of other suitable $R_1$ groups are alkyl groups, cycloalkyl groups, and groups containing heteroatoms, such as oxygen, sulphur, nitrogen, etc. Generally the $R_1$ groups contain from 1 to 22 carbon atoms, preferably 1-12 carbon atoms; and in conjunction with Y—Ar, they must absorb radiation between 250-800 nm. range.

Examples of some alkyl groups are methyl, ethyl, t-butyl, t-amyl, hexyl, 2-ethylhexyl, nonyl and octadecyl.

Examples of some suitable aryl groups include phenyl, phenanthryl, and anthracyl.

Examples of some cycloalkyl radicals include cyclopropyl, cyclopentyl, cyclobutyl, cyclohexyl, cycloheptyl, cyclooctyl, and cyclododecyl.

Examples of some aralkyl groups are phenylmethyl and naphthylethyl.

Examples of some alkaryl groups include tolyl, xylyl and cumyl.

Examples of substituted aryl groups in addition to alkaryl include alkoxy-substituted aryl groups, such as methoxyphenol. The substituted aryl groups usually contain 1, 2 or 3 substitutions which are usually ortho and/or para with respect to the carbonyl group to which the substituted aryl group is connected.

The heterocyclic groups generally contain 5-6 members in the ring and contain S, O and/or N in the ring and include morpholinyl, piperidyl, thiophenyl, and furanyl.

The preferred $R_1$ groups are aryl and substituted aryl groups and the most preferred $R_1$ groups are phenyl and alkyl and/or alkoxy-substituted phenyl wherein the alkyl and/or alkoxy groups contain 1 to 22 carbon atoms and preferably 1-12 carbon atoms.

The two carbonyl groups located on the benzene rings can be ortho, meta, or, preferably, para to each other.

The synthesis was based on a general perester of the formula:

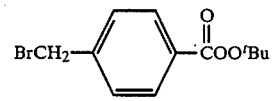

Formula I

The initiators of interest are, with the exception of Formula II, non-conjugated peresters based on pyrene, anthracene, and fluorenone as indicated below.

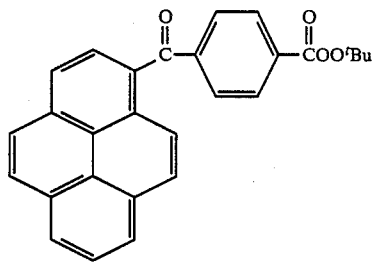

Formula II

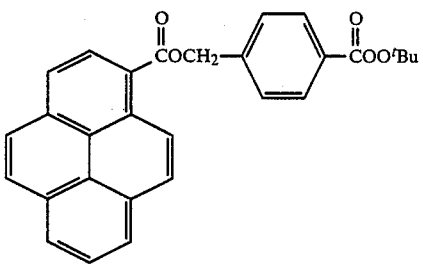

Formula III

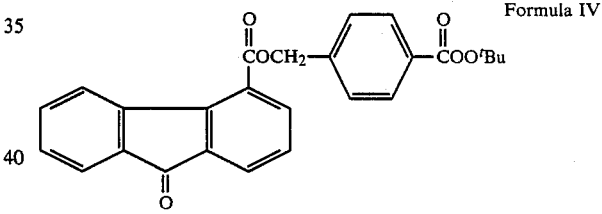

Formula IV

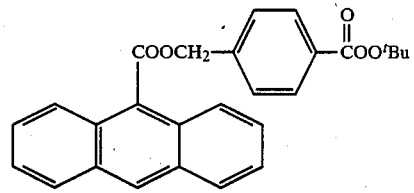

Formula V

The compounds of the present invention can be readily obtained from the corresponding carboxylic acids. In particular, the corresponding carboxylic acid can be reacted at elevated temperature (e.g. up to about 60° C.), preferably at reflux, with, for example, thionyl chloride to form the corresponding acid chloride. Next, the acid chloride can be reacted with a hydroperoxide, such as tert-butyl hydroperoxide in the case of R being t-butyl, usually in the presence of a tertiary amine, preferably triethylamine. In addition, it is preferred that this stage of the preparation be carried out in the presence of a diluent, such as ether, benzene, or dichloromethane.

The compounds of the present invention are especially useful as photoinitiators in the polymerization of photopolymerizable ethylenically unsaturated materials. The photopolymerizable materials can be monomeric or prepolymers containing one or more ethylenically unsaturated groups.

Examples of some suitable photopolymerizable materials include esters of unsaturated monocarboxylic acids or dicarboxylic acids, e.g. esters of acrylic acid, methacrylic acid, α-cyanacrylic acid, sorbic acid, fumaric acid or itaconic acid with aliphatic, cycloaliphatic or aromaticaliphatic monohydric to tetrahydric alcohols of 3 to 20 carbon atoms, e.g. methyl acrylate and methacrylate; n-, i- and t-butyl acrylate and methacrylate; 2-ethylhexyl acrylate; lauryl acrylate; dihydrodicyclopentadienyl acrylate and methacrylate; methylglycol acrylate; hydroxyethyl acrylate and methacrylate; hydroxypropyl acrylate and methacrylate; ethylene glycol diacrylate; diethylene glycol diacrylate; triethylene glycol diacrylate; neopentylglycol diacrylate and dimethacrylate; 1,4-dimethylolcyclohexane diacrylate; pentaerythritol-triacrylate, -tetraacrylate, -trimethacrylate and -tetramethacrylate; ethyl α-cyanacrylate; ethyl crotonate, ethyl sorbate; diethyl fumarate; and the diacrylate and dimethacrylate or oxyalkylated bisphenol A; amides of acrylic acid or methacrylic acid which may or may not be substituted at the nitrogen by alkyl, alkoxyalkyl or hydroxyalkyl, e.g., $N_1N'$-di-methacrylamide, N-isobutylacrylamide, diacetonaecrylamide; N-methylolacrylamide, N-methoxymethylacrylamide, N-butoxymethylacrylamide, N-butoxymethylmethacrylamide and ethylene glycol bis(N-methylolacrylamide)ether; vinyl esters of monocarboxylic acids or dicarboxylic acids of 2 to 20 carbon atoms, e.g., vinyl acetate, vinyl propionate, vinyl 2-ethylhexanoate, vinyl versatate and divinyl adipate; vinyl ethers of monohydric or dihydric alcohols of 3 to 20 carbon atoms, e.g., isobutyl vinyl ether, hexyl vinyl ether, octadecyl vinyl ether, ethylene glycol divinyl ether, diethylene glycol divinyl ether, butanediol divinyl ether and hexanediol divinyl ether; mono-N-vinyl compounds, e.g., N-vinyl-pyrrolidone, N-vinylpiperidone, N-vinylcaprolactam, N-vinylmorpholine, N-vinyloxazolidone, N-vinylsuccinimide, N-methyl-N-vinylformamide and N-vinylcarbazole; allyl ethers and allyl esters, e.g., trimethylolopropane diallyl ether, trimethylolpropane triallyl ether, pentaerythritol triallyl ether, diallyl maleate, diallyl fumarate or diallyl phthalate; vinyl and vinylidine halides, e.g., vinyl chloride and vinylidene chloride; and vinyl aromatics, e.g., styrene, alkyl styrenes, halostyrenes and divinylbenzenes.

Examples of some polymeric photopolymerizable materials include unsaturated polyesters obtained, for instance, from α, β-unsaturated dicarboxylic acids, e.g., maleic acid, fumaric acid or itaconic acid, and aliphatic, cycloaliphatic or non-phenolic aromatic diols, e.g., ethylene glycol, diethylene glycol, triethylene glycol, propane-1,2-diol, propane-1,3-diol, butane-1,2-diol, butane-1,3-diol, butane-1,4-diol, but-2-ene, 1,4 diol, neopentylglycol, hexane-1,6-diol or oxyalkylated bisphenol A; unsaturated epoxide-acrylates obtained, for instance, from monofunctional epoxides and acrylic acid of methacrylic acid, by the method of U.S. Pat. No. 2,484,487, bifunctional epoxides and unsaturated fatty acids, by the method of U.S. Pat. No. 2,456,408 polyfunctional aromatic epoxides and crotonic acid, by the method of U.S. Pat. No. 2,575,440 or polyfunctional aromatic or aliphatic fatty glycidyl ethers and acrylic acid or methacrylic acid, by the method of U.S. Pat. No. 2,842,851; unsaturated polyurethanes (urethaneacrylates) prepared from hydroxyalkyl acrylates and diisocyanates, with or without polyols or polyamines; unsaturated copolymers, prepared, for example, by reacting copolymers, containing maleic anhydride groups, with unsaturated alcohols; or acrylic ester copolymers containing carboxylic acid groups or polyesters containing carboxylic acid groups with unsaturated epoxides, e.g., glycidyl acrylates; butadiene polymers in which the double bonds are predominantly present as vinyl side chains; diallyl phthalate prepolymers; and poly-N-vinylurethanes, e.g. prepared, for instance, by reacting vinyl isocyanate with saturated or unsaturated polyesterpolyols, polyether-polyols or polyfunctional alcohols.

The peresters when employed as photoinitiators are usually present in amounts of about 1 to about 10%, and more usually about 1 to about 3% by weight based upon the weight of the photopolymerizable material present. The polymerization of such compositions can be carried out by subjecting or exposing the compositions to light (e.g., UV or visible) of appropriate wavelength absorbable by the chromophore moiety of the perester employed. The compounds of the present invention can be tailored by the particular chromophore group present to provide light absorption properties for a given wavelength selected from a broad spectrum of wavelengths, preferably in the visible and UV ranges. It is preferred that the chromophore group be selected so that it absorbs light in the range of about 250–800 nm. The particular wavelength to employ is determinable by those skilled in the art without undue experimentation once they are aware of the present invention and the particular chromophore group present.

Polymers obtained from polymerization in the presence of the peresters of the present invention have been found to contain as end group the chromophore group from the perester employed; and, therefore, can subsequently be subjected to irradiation to achieve some crosslinking.

Polymerization of the composition usually requires exposure to the light for about 30 seconds to about 10 minutes depending upon the amount of initiator present. The time and amount are inversely related. The crosslinking reaction is usually about $10^2$ to $10^3$ times slower than the polymerization and usually requires about 1 to about 20 hours depending upon the amount of initiator employed.

The followihg non-limiting examples are presented to further illustrate the present invention:

Example 1—Preparation of peresters

Starting materials and other reagents were obtained from Aldrich Chemical Company and purified, where necessary, by standard procedures. The monomers, MMA and styrene, were freed of inhibitor by washing with a 5% NaOH solution followed by repeated washing with distilled water. The monomers were then dried and distilled under reduced pressure just prior to use. All melting points are uncorrected. Ultraviolet spectra were obtained on a Varian Model 219 spectrometer. The intensity of the radiation was monitored constantly by benzophenone/benzhydrol actinometry at 30° and observed to be $9.15 \times 10^{17}$ quanta/minute, as described by L. Thijs, S. N. Gupta and D. C. Neckers, *J. Org. Chem.* 44, 4123 (1979).

4-Bromomethyl Benzoyl Chloride and -peroxybenzoic acid, tert-Butyl Ester (Crucial Perester Intermediate Formula I)

4-Bromomethyl benzoic acid (18.53 g., 0.086 moles) which had been prepared by the Tuleen method, D. L.

Tuleen and B. A. Hes, *J. Chem. Ed.* 40, 476 (1971), and finely powered was refluxed for one hour with an excess of thionyl chloride and a few drops of pyridine. A rapid evolution of hydrogen chloride took place for a few minutes and then stopped. Excess thionyl chloride was distilled off under vacuum and the oily residue dissolved in hexane. Crystallization occurred soon in the refrigerator. Filtration gave 14.32 g (71% yield) of the acid chloride.

Preparation of Formula I Perester

To an ice-salt cooled solution of 13.22 g (56 mmols) of 4-bromomethyl benzoyl chloride in 125 ml of dry ether was added dropwise over 30 minutes under magnetic stirring a solution of 5.45 g (60 mmole) of tert-butyl hydroperoxide and 6.56 g (65 mmoles) of triethylamine in 50 ml of ether. After the addition of mixture was stirred for another hour. Filtration and evaporation left a solid. This was dissolved in dichloromethane and chromatographed over silica gel with dichloromethane as eluent. This gave 16.46 g of a colorless perester (90% yield) which was further purified by vacuum sublimation. The pure sample melted at 93°-4°. IR(KBr) 1760 cm$^{-1}$ ($\nu$ C=O perester)

NMR (CDCL$_3$)

$\delta$=1.44 s 9H CH$_3$; 4.52, s 2H, CH$_2$; 7.44–8.00, 9H aromatics

Synthesis of 4-[(1-Pyrenyl)carbonyl]-Peroxybenzoic Acid, tert-Butyl Ester Formula II Pyrene, (6.75 g; 0.033 mol) was dissolved in 75 ml of dry benzene. 4-Carbomethoxybenzoyl chloride (6.0 g; 0.030 mol) was added. To this solution 6.75 g (0.050 mol) of aluminum chloride was gradually added. A dark color developed. After the addition of AlCl$_3$ the temperature increased slightly and then the temperature of the mixture was increased to 40° with a water bath and gradually recooled to room temperature. The reaction mixture was then poured into an ice bath to which 5 ml of HCl had been added. The benzene was removed by steam distillation. The organic mixture was extracted with benzene and dried over magnesium sulfate. The solvent was evaporated and the residue chromatographed on silica gel with hexane. Elution with carbon tetrachloride gave pyrene, 3.2 g. Elution with carbon tetrachloride/chloroform (1:2) gave a yellow solid in two fractions (1.62 g; 3.25 g). The former fraction contained some pyrene. The latter fraction was extracted with hot ethanol to give 2.55 g of a yellow solid (mp. 141°-144°), identified as 4-[(1-pyrenyl)carbonyl]benzoic acid methyl ester. From the 1.62 g in fraction one of the eluted ketone, 1.01 g was obtained.

4-[(1-Pyrenyl)carbonyl]benzoic acid, methyl ester (2.55 g; 7 mmol) was dissolved in 25 ml of benzene. A solution of 354 mg (6.4 mmol) of KOH in 5 ml MeOH was added, and the mixture boiled. Precipitation of the potassium salt occurred. The mixture was extracted with water to give a yellow water layer which was acidified with dilute HCl to give a light yellow precipitate. Filtration gave 1.73 g (5 mmol) of the 4-[(pyrenyl)-carbonyl]benzoic acid.

IR 3600-3350 cm$^{-1}$; 1710 cm$^{-1}$; 1665 cm$^{-1}$.

4-[(1-Pyrenyl)carbonyl]benzoic acid (1.73 g; 5 mmol) was refluxed with 10 ml of SOCl$_2$ and 3 drops of pyridine for 3 hours. A yellow/brown solution resulted. The excess thionyl chloride was evaporated and the residue triturated with ether/hexane and filtered to give the yellow acid chloride.

IR: 1652 cm$^{-1}$; 1770 cm$^{-1}$.

The acid chloride was dissolved in 60 ml of a benzene/chloroform mixture (50/10) and a mixture of tert-butyl hydroperoxide (5.2 mmol) and triethylamine (606 mg; 6 mmol) was added. After the addition the mixture was stirred for 2 hours at room temperature and then heated to 50° for a few minutes.

The solvent was evaporated and the residue dissolved in dichloromethane and chromatographed over silica gel. Elution with CH$_2$Cl$_2$ gave a yellow band which oiled when the solvent contained no perester. Elution was continued in the dark to give 1.50 g of a dark yellow oil which, when heated with cyclohexane/benzene dissolved. After several days in the refrigerator light yellow crystals formed which analyzed as the Formula II perester.

IR 1660 cm$^{-1}$ ($\nu$ C=O ketone); 1770 cm$^{-1}$ ($\nu$ C=O adjacent to perester)

NMR (CDCl$_3$) $\delta$=1.43, s, 9H; CH$_3$ $\delta$=7.9–8.4 m, 13 H; aromatic protons Analysis: Calc. for C$_{28}$H$_{22}$O$_4$: C=79.55; H=5.25 Found: C=79.40; H=5.32

4-[(1-Pyrenyl)carbonyloxymethyl]Peroxybenzoic Acid, tert-Butyl Ester (Formula III)

Pyrene-1-carboxylic acid (1 g, 4 mmoles) was converted into the dry potassium salt as previously described. A suspension of the potassium salt, 0.65 g of the bromomethyl Formula I perester (2 mmoles) and 60 mg of 18 crown-6- (0.23 mmoles) was stirred for 60 hours in the dark. Evaporation and chromatography of the residue over silica gel with carbon tetrachloride/chloroform 1:1 as eluent gave 1.0 of yellow oil. Recrystallization from cyclohexane gave 0.82 g of crystals, m.p.=105°-08°. Another recrystallization raised the melting point 2°.

IR (KBr) 1750 cm$^{-1}$ ($\nu$ C=O adjacent to perester) 1720 cm$^{-1}$ ($\nu$ C=O ester)

NMR (CDCl$_3$)

$\delta$=1.41, s, 9H, CH$_3$ $\delta$=5.56, s, 2H, CH$_2$ $\delta$=7.55–9.32, m, 13H aromatic protons with a doublet for one proton at $\delta$=9.26, a doublet for another proton at $\delta$=8.64 and a doublet for 2 protons at $\delta$=7.61 apparent as part of an AB system.

Analysis: Calc; C=76.99; H=5.31 Found: C=76.81; H=5.39

Preparation of 4-[(9H-fluorenone-9-one-4-yl)carbonyloxymethyl]-Peroxybenzoic Acid, tert-Butyl Ester (Formula IV)

4-Carboxyfluorenone (896 mg, 4 mmoles) was treated was a suspension in 50 ml water with an equivalent amount of KOH solution (224 mg KOH; approximately 4 mmoles; pH of the solution close to 7.0). Filtration removed the small amount of undissolved solid and the obtained filtrate was evaporated to dryness. The so obtained potassium salt of the acid was thoroughly dried in an Abderhalen drying apparatus. A suspension was made of the potassium salt in 10 ml of dry acetonitrile and 0.65 of the 4-bromomethyl Formula I perester (2 mmoles) and 60 mg of 18-crown-6 (0.23 mmoles) added. The mixture was stirred for 16 hr. in the dark while the progress of the reaction followed by TLC. Evaporation and chromatography, on silica gel with 1:1 carbon tetrachloride/chloroform as the eluting solvent gave 0.85 g of the perester as a yellow oil. Recrystallization from cyclohexane gave yellow crystals, mp. 102°–104°.

IR (KBr):
1750 cm$^{-1}$ ($\nu$ C=O adjacent to perester);
1725 cm$^{-1}$ ($\nu$ C=O ester);
1710 cm$^{-1}$ ($\nu$ C=O ketone).
Analysis: Calc; C=72.56, H=5.11 Found: C=72.65; H=5.15
NMR: (CDCl$_3$)
$\delta$=1.4, s, 9H, methyl
$\delta$=5.4, s, 2H, methylene
$\delta$=7.49–8.03, m, 11H aromatic protons 4-[(9-Anthryl)Carbonyloxymethyl]Peroxybenzoic Acid, tert-Butyl Ester Formula V Anthracene-9-carboxylic acid (888 mg., 4 mmol) was converted to the dry potassium salt by the same procedure as above. As suspension of the potassium salt in 10 ml of dry acetonitrile was stirred over the weekend with 0.65 g (2 mmol) of the bromomethyl Formula I perester, and 60 mg (10.23 mmol) of 18-crown-6.

Evaporation and chromatography of the residue as before with carbon tetrachloride/chloroform (1:1) gave a yellow oil (0.82 g.). Recrystallization from cyclohexane gave 0.58 g of yellow crystals; m.p. 118°–119°.

IR (KBr) 1750 cm$^{-1}$ ($\nu$ C=O adjacent to perester 1720 cm$^{-1}$ ($\nu$ C=O ester)
NMR: (d-benzene)
$\delta$=1.70, s, 9H, CH$_3$
$\delta$=5.28, s, 2H, CH$_2$
$\delta$=7.18–8.09, m, 13H, aromatic protons Example 2—Decomposition of Peresters By Irradiation and Kinetics Thereof Photopolymerizations Photopolymerizations were carried out in sealed, degassed tubes (12 mm diameter) by irradiation at 366 nm with a high pressure mercury arc. All irradiation techniques were identical to those previously reported in I.I. Abu-Abdoun, L. Thijs and D. C. Neckers, *J. Poly Sci., Chem Ed., J. Med. Chem. Society*, Vol. 21, p. 3129, September, 1983. After the irradiation period, the polymers obtained were precipitated in methanol and analyzed gravimetrically (Abu-Abdoun et al.).

Initiator concentrations for the bulk polymerizations were $2.4 \times 10^{-3}$ mol/l and in the case of solution polymerizations varied as specified in the particular experiment.

Polymer molecular weights were determined in dichloromethane using a Waters Associate Model 440 GPC, and were calculated from elution volumes with reference to polystyrene standards. These standards were used for calibration at a solvent flow rate of 1.5 ml/min. and a polymer concentration of 1 mg/ml, by the method of U.S. Pat. No. 4,416,826.

A series of peresters based on aromatic chromophores which absorb radiation at about 366 nm but which do not produce $\eta$-$\pi$ * excited triplet states upon absorption are reported. Three of the peresters were synthesized from crucial intermediate bromomethyl Formula I perester by nucleophilic displacement of bromide ion. One of the Formula II peresters was synthesized directly from the appropriate carboxylic acid by a Friedel Crafts process. A series of routine nucleophilic displacement reactions is carried out on perester containing an appropriate leaving group without disturbing the —O—O— bond of the perester unit. The physical and spectroscopic parameters of the peresters designed are reported in Table 1.

TABLE 1

Characteristics of Formula II, III, IV and V Peresters

| Perester Structure | Extinction Coefficient at 366 nm in CH$_2$Cl$_2$ 1 mol$^{-1}$ cm$^{-1}$ | m.p. °C. | Yield % |
|---|---|---|---|
| Fluorenone perester (Formula IV) | $2.73 \times 10^2$ | 102–104 | 79 |
| Anthracene perester (Formula V) | $8.3 \times 10^3$ | 118–119 | 68 |
| Pyrene ketone perester (Formula II) | $1.0 \times 10^4$ | 122 | 65 |
| Pyrene ester perester (Formula III) | $1.82 \times 10^4$ | 107–109 | 80 |

Uv spectra for the peresters synthesized are shown in FIG. 1.

In every respect, the compounds reflect the photochemistry and the spectroscopy of the parent chromophore except that they are coupled to a tert-butyl perester functionality, either conjugated directly, or insulated by at least one methylene group included in the molecule. For these peresters to be useful photoinitiators they must absorb a light quantum and convert the derived energy to a bond homolysis reaction producing a tert-butoxy and an aryloxy free radical pair. G. Sosnovsky, *Free Radical Reactions in Preparative Organic Chemistry*, Mac Millan, N.Y., (1964); C. Ruchardt, *Angew Chem. Intern. Edt.* 9, 930 (1970).

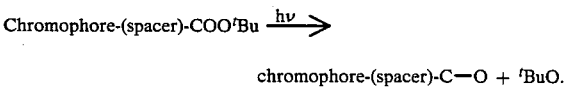

Chromophore-(spacer)-COO$^t$Bu $\xrightarrow{h\nu}$ chromophore-(spacer)-C—O + $^t$BuO.

The ability of the photoinitiators in Table 1 to produce free radicals which initiate vinyl polymerization was studied by measuring the rate of polymerization of methyl methacrylate and styrene under identical conditions of light intensity, initiator concentration, monomer concentration and temperature. The conversion versus time curves for the photopolymerization of methyl methacrylate using these initiators are given in FIG. 2. As is shown in FIG. 2, the rate of MMA photopolymerization decreases in the following sequence of perester structure: fluorenone > pyrene ketone > pyrene ester > anthracene.

Figure 3:
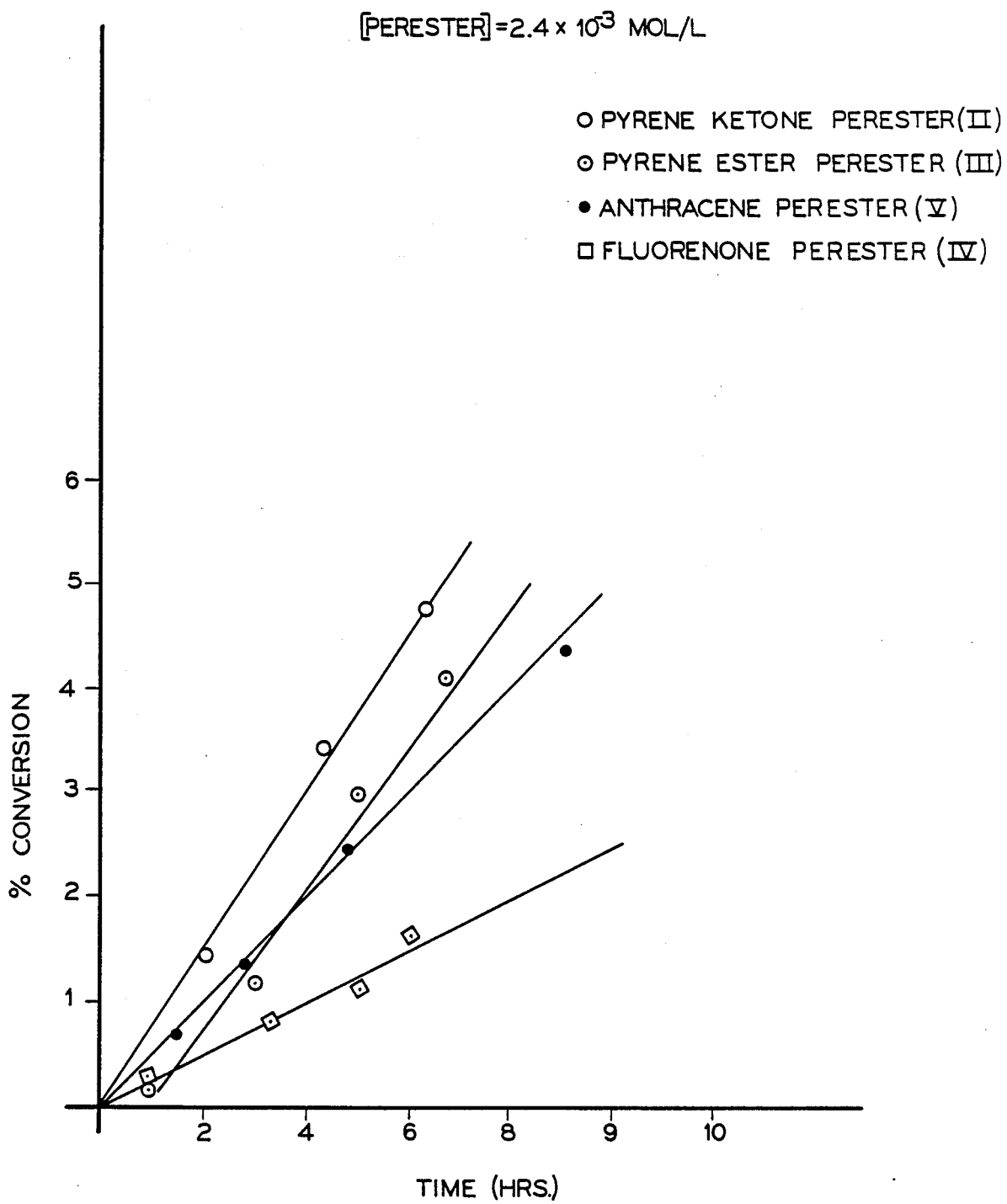
FIG. 3 is a graph showing photopolymerization of styrene (bulk) initiated by various peresters.

The photoinitiation of styrene initiated by each of these peresters was carried out similarly and is shown in FIG. 3. The rate of styrene photopolymerization decreased in the following order: pyrene ketone > pyrene ester > anthracene > fluorenone.

Figure 2:
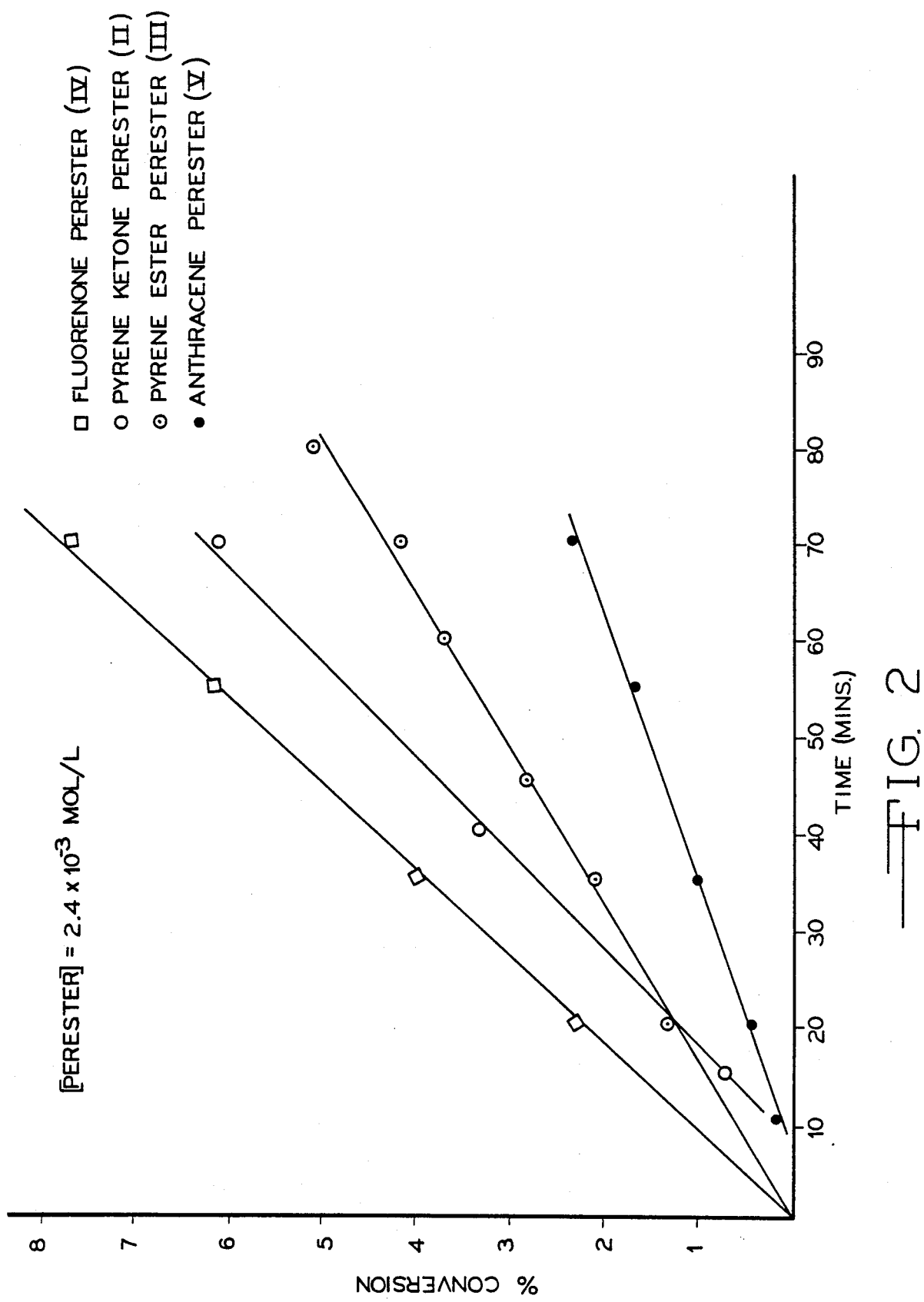
FIG. 2 is a graph showing photopolymerization of MMA (bulk) initiated by various peresters.

It is clear from FIG. 2 and FIG. 3 that the reactivity order of these aromatic peresters depends on the type of monomer being polymerized. Thus in the polymerization of MMA, the fluorenone perester, Formula IV, is the fastest, whereas in the polymerization styrene, it is the slowest. The rates of polymerization—at identical times for the two monomers, MMA and styrene, are compared in Table 2.

TABLE 2

Photo Polymerization (Bulk) of Vinyl Monomers Initiated by Various Peresters

| Initiator | After 60 mins. MMA Rp mol $1^{-1}$ sec$^{-1}$ | After 3 hrs. Styrene Rp mol $1^{-1}$ sec$^{-1}$ |
|---|---|---|
| Pyrene ester perester (Formula III) | $1.1 \times 10^{-4}$ | $1.95 \times 10^{-5}$ |
| Pyrene ketone perester (Formula II) | $1.54 \times 10^{-4}$ | $2.44 \times 10^{-5}$ |
| Fluorenone perester (Formula IV) | $1.92 \times 10^{-4}$ | $9.8 \times 10^{-6}$ |
| Anthracene perester (Formula V) | $5.63 \times 10^{-5}$ | $1.22 \times 10^{-5}$ |

Effects of Monomer and Perester Concentration on the Polymerization Rate

Figure 4:
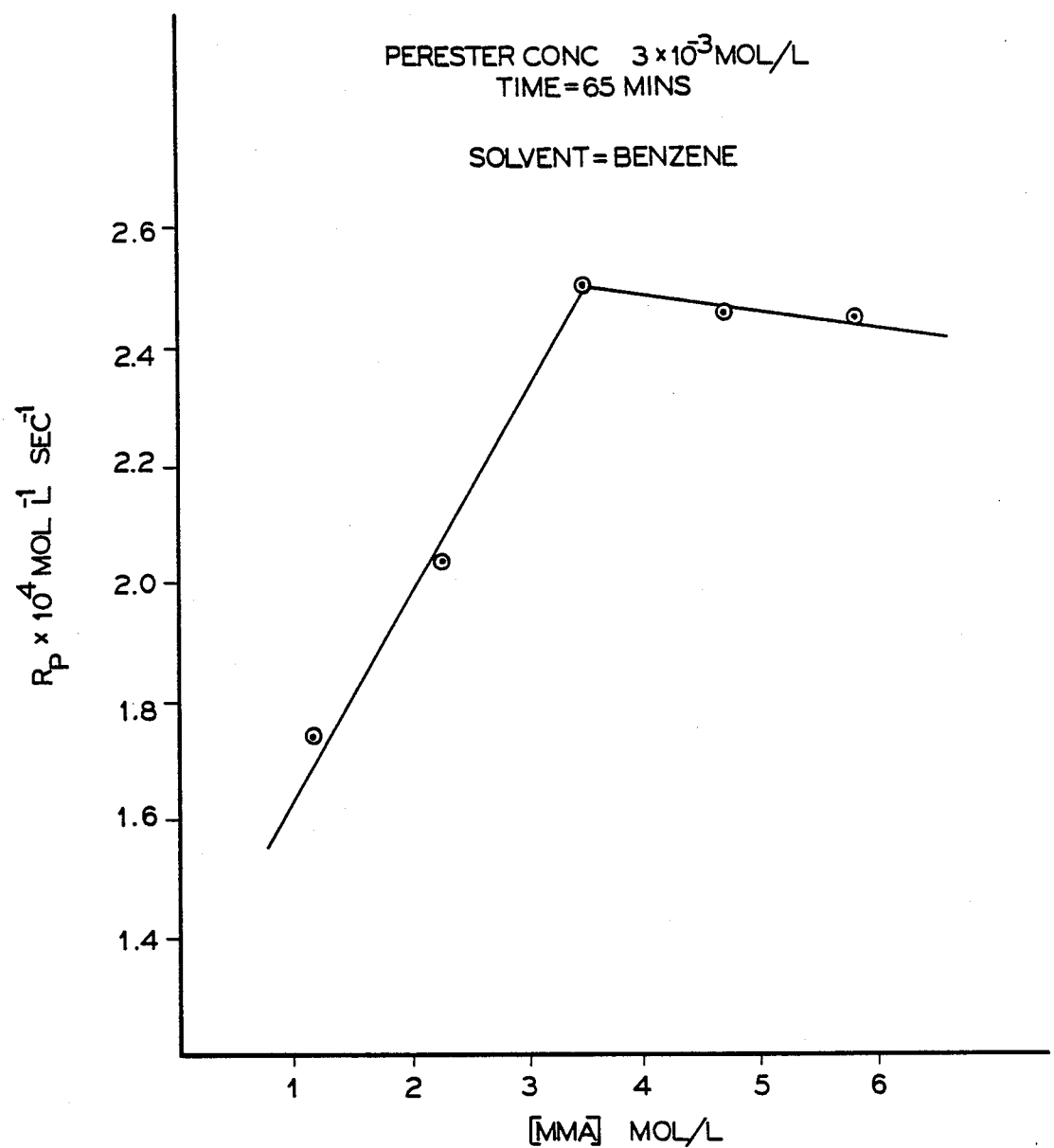
FIG. 4 is a graph showing photopolymerization of MMA initiated by fluorenone perester (Formula IV).

The relationship between the rate of polymerization, Rp, and the concentration of the monomer is a function of both the structure of the initiator and the monomer being polymerized. Thus the Rp of MMA with fluorenone perester, Formula IV, as the initiator increases to a maximum as the monomer concentration is increased (to about 3.5M in benzene) and then levels off, as seen in FIG. 4.

Figure 5:
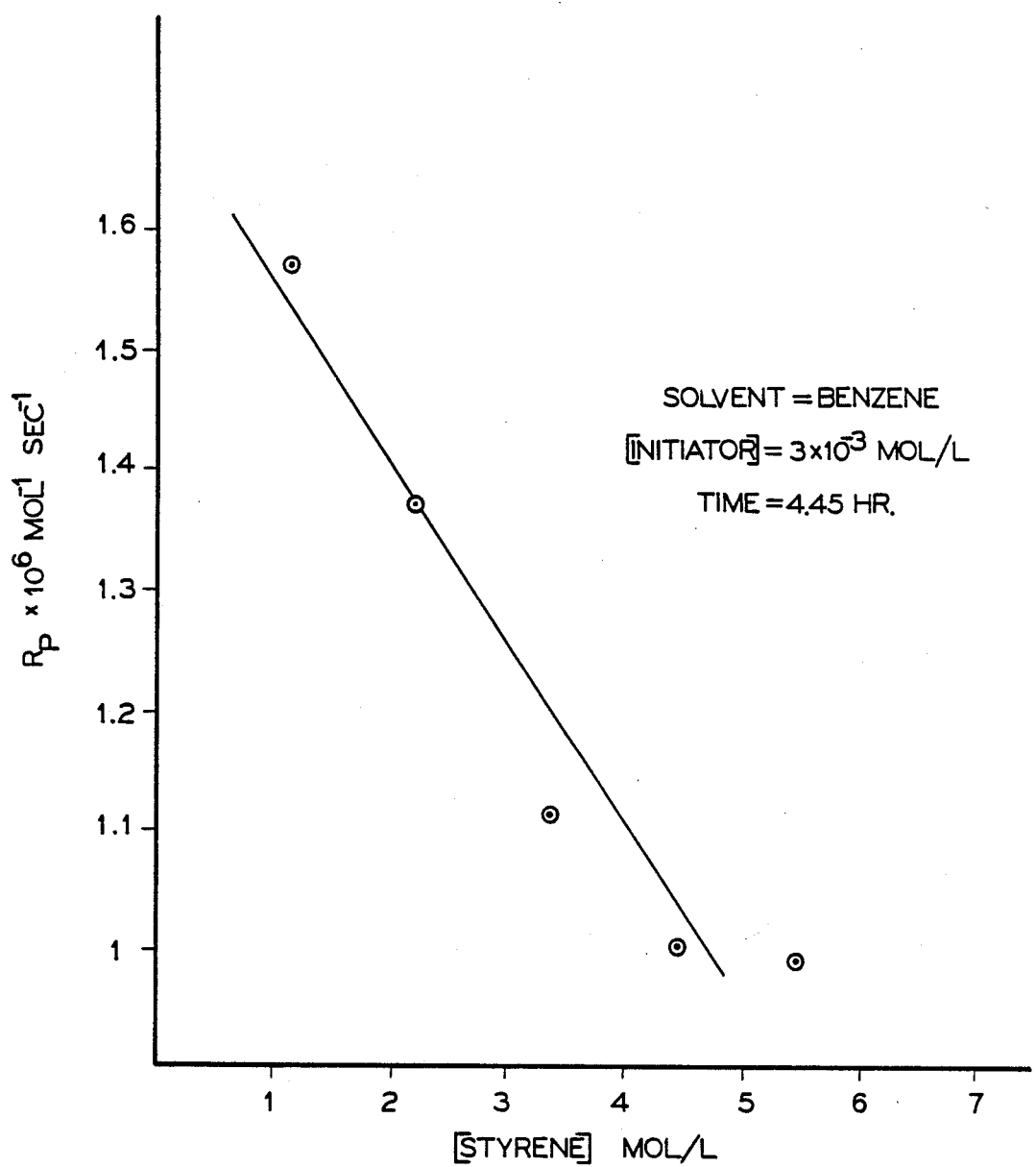
FIG. 5 is a graph showing photopolymerization of styrene initiated by fluorenone perester (Formula IV).

For styrene photopolymerization utilizing the same initiator, the concentration of styrene increases the rate of polymerization decreases, as seen in FIG. 5.

In this instance either the excited state of the initiator is quenched by the monomer, or the monomer reacts with the initiator before bond homolysis occurs.

Figure 6:
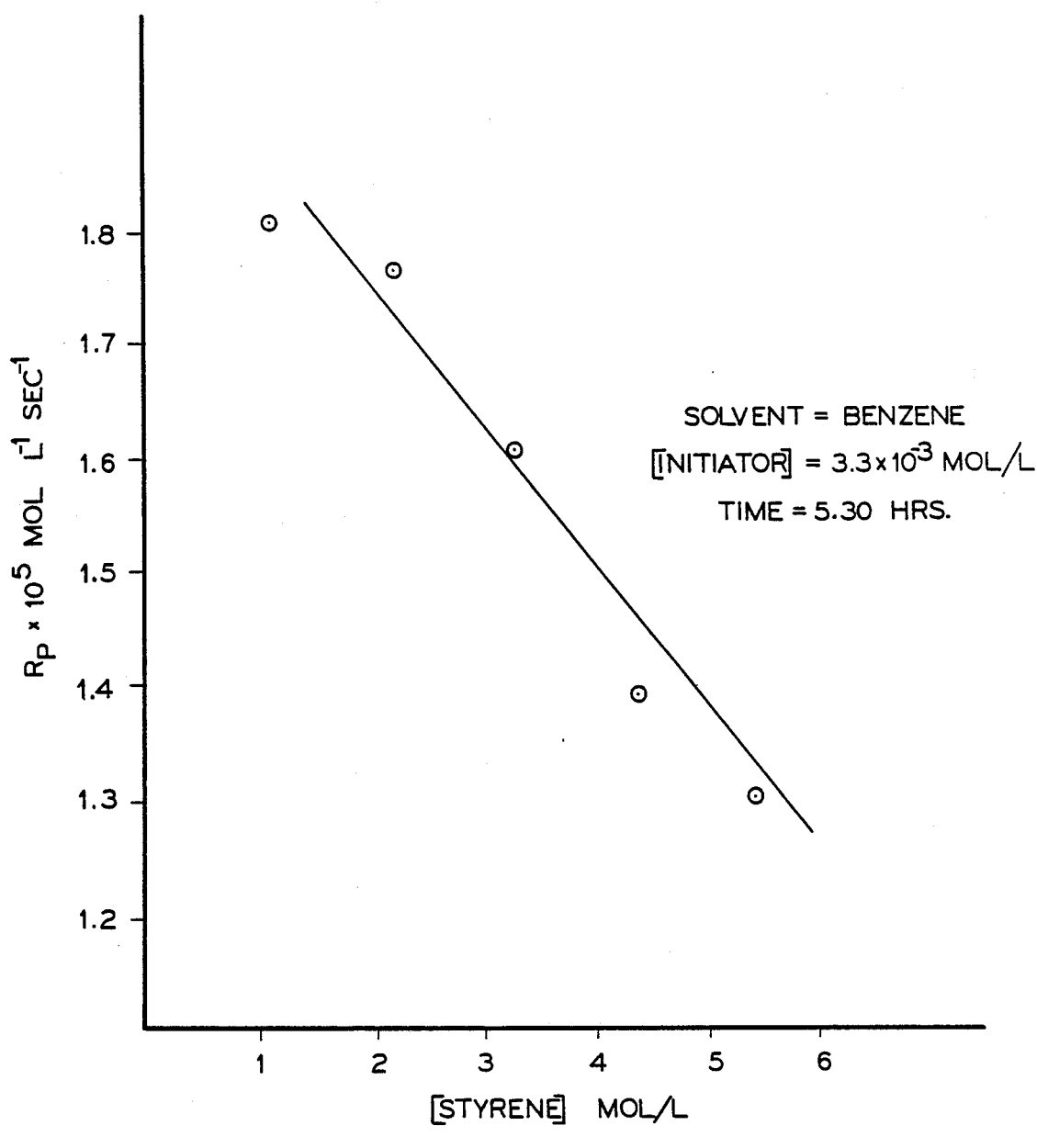
FIG. 6 is a graph showing photopolymerization of styrene by pyrene ketone perester (Formula II).

Formula II and Formula III peresters present test cases by means of which the localization of energy in the excited state is assessed. The keto pyrene perester, Formula II, is quenched by styrene or at least the rate of polymerization decreases as the styrene concentration is increased, as seen in FIG. 6.

Figure 7:
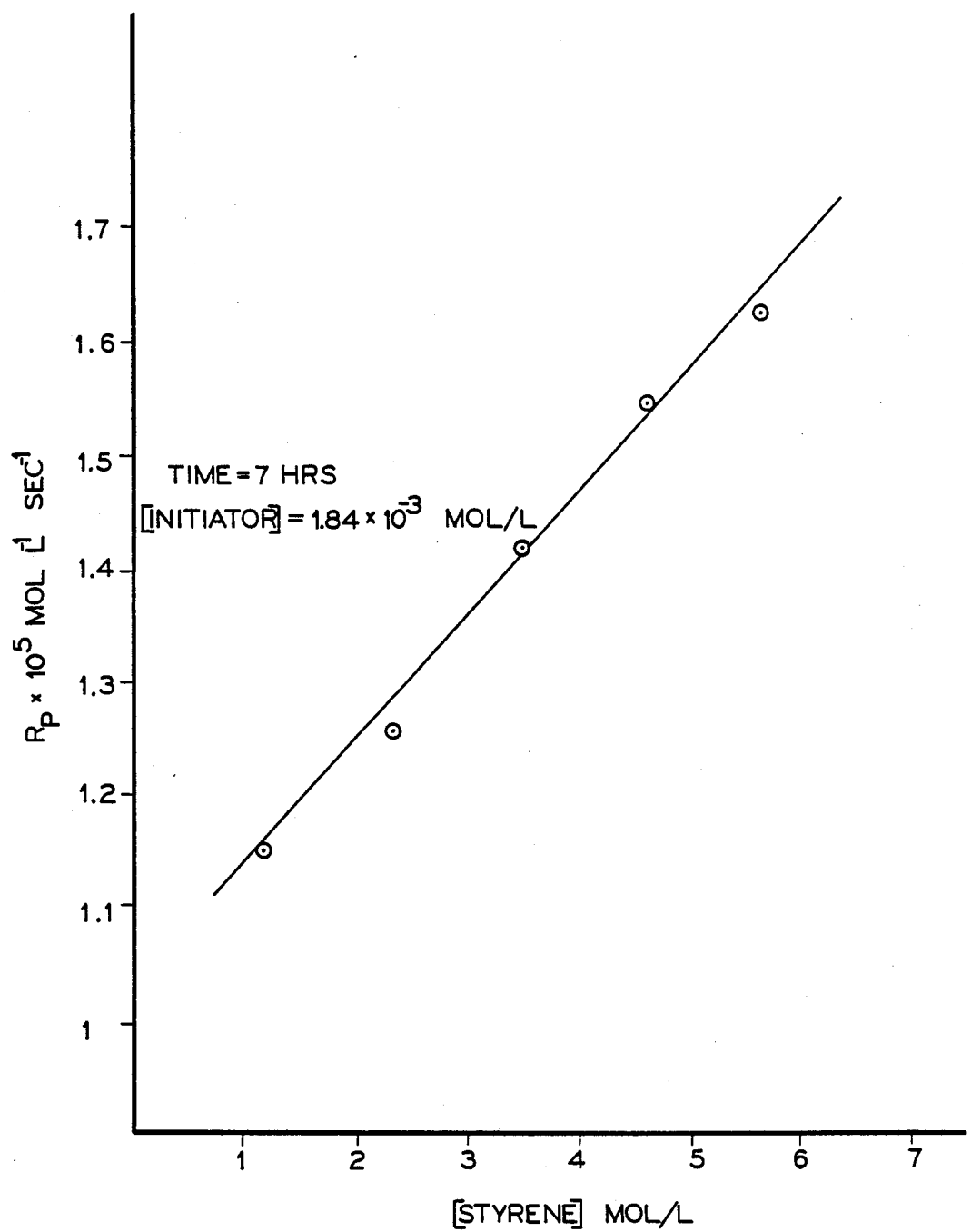
FIG. 7 is a graph showing dependence of the photopolymerization rate (Rp) of styrene on the monomer concentration in benzene for pyrene ester perester (Formula III).

The non-ketonic pyrene photoinitiator, Formula III, behaves more normally with the rate of styrene polymerization actually increases with concentration of monomer when it is used, as seen in FIG. 7.

Styrene solutions of the non-ketonic pyrene initiator, Formula III, fluoresce while being irradiated in the monomer (styrene or MMA) for the purpose of studying them as photoinitiators, while the ketonic pyrene systems (Formula II) are non-emitting under identical conditions.

Figure 8:
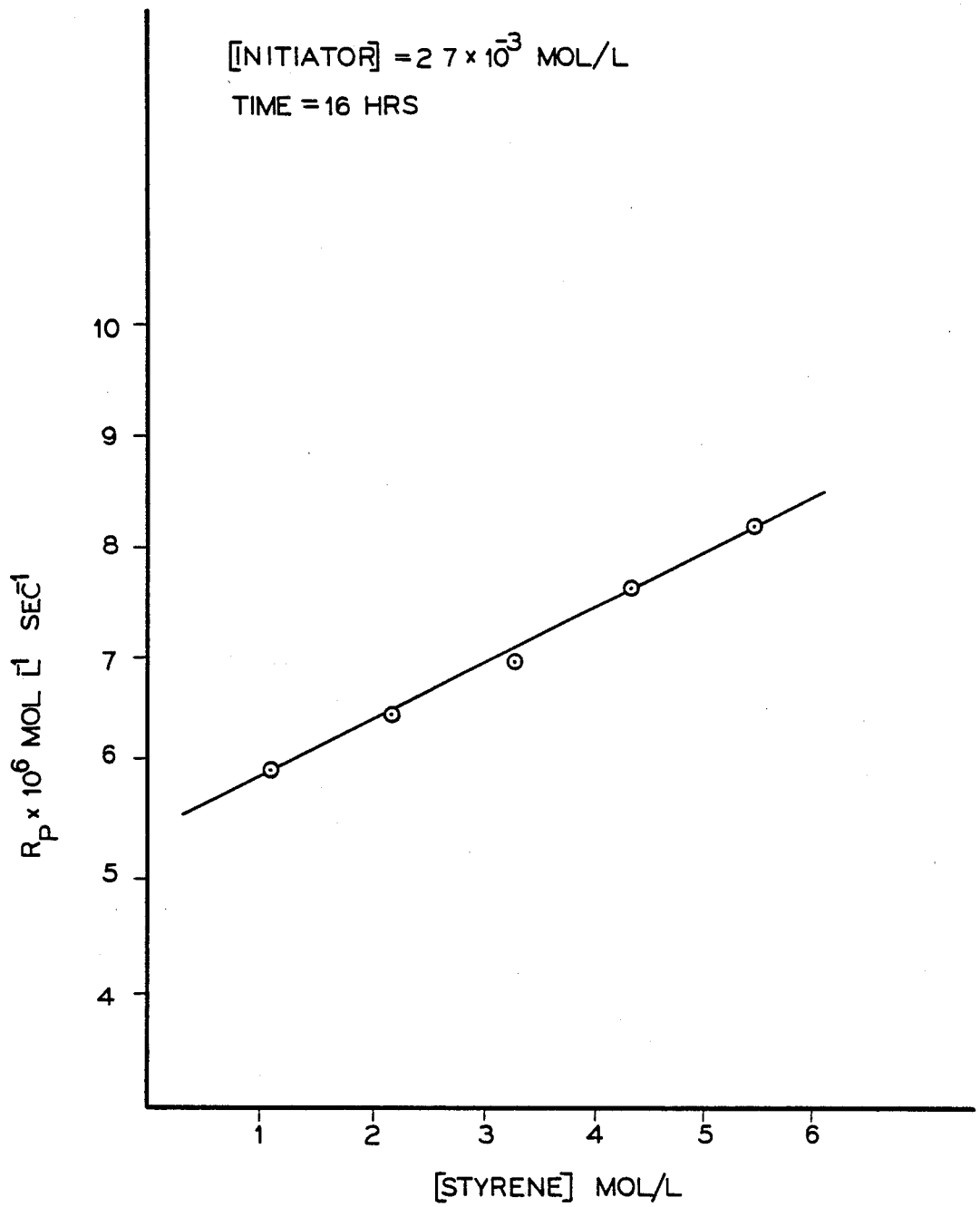
FIG. 8 is a graph showing dependence of the photopolymerization rate (Rp) of styrene on the monomer concentration for anthracene perester (Formula V).

FIG. 8 shows the rate of photopolymerization of styrene as a function of styrene concentration initiated by another $\pi$-$\pi$* photoinitiator, the anthracene derivatives, Formula V. As in the case of the pyrene perester, Formula III, the anthracene system is not quenched by styrene and the Rp increasing with increasing styrene concentration.

Figure 9:
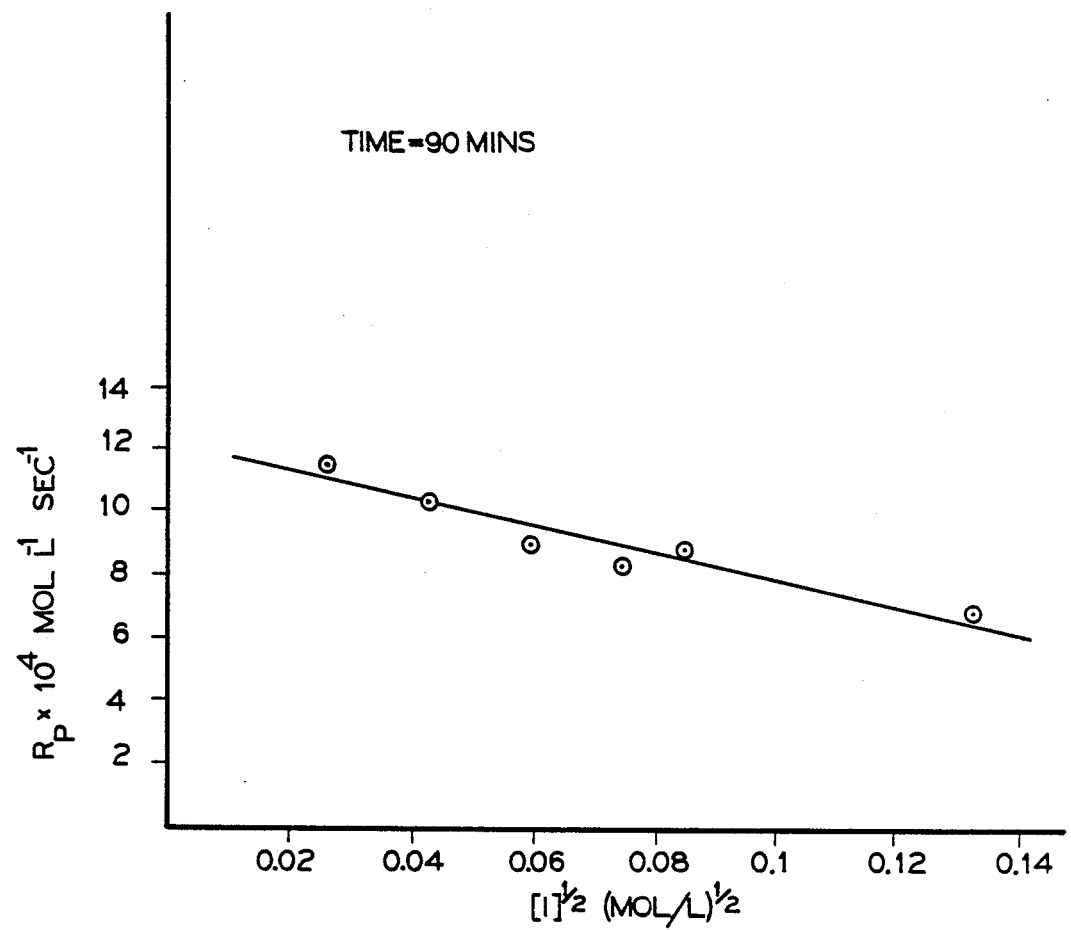
FIG. 9 is a graph showing dependence of the photopolymerization rate (Rp) of MMA on the initiator concentration for pyrene ester perester (Formula III).

The effect of initiator concentration on the rate of polymerization is determined by the termination step of the radical chain as described by S. Gupta, I. Gupta and D. C. Neckers, *J. Poly. Sci., Poly. Chem. Ed.* 19, 103 (1981), and is half order in initiator when termination is bimolecular in chain fragments. The rate, as a function of initiator concentration, also is a function of self-quenching of initiator excited states. Thus, the way the rate of polymerization of MMA could decrease as a function of pyrene perester concentration, as seen in FIG. 9, is if the excited state of the perester were quenched either by another perester ground state, or by a perester residue in a polymer chain. Increasing the initiator fragments in the system increases the possibility of chromophore self-quenching and decreases the rate of initiation at higher concentrations of photoinitiator.

Effect of Monomer and Perester Concentration on the Molecular Weight of the Polymer Table 3 and Table 4 show the effect of polymerization time and the structure of the aromatic perester photoinitiator on the molecular weight of the derived polymer, both in the case of methyl methacrylate and styrene.

TABLE 3

Photopolymerization of MMA (Bulk) Initiated by Various Peresters Molecular Weight Dependence on Initiator Structure and Polymerization Time

| Initiator | Polymerization Time (Mins.) | Mn (average) |
|---|---|---|
| Pyrene ketone perester (Formula II) | 40 | $1.7 \times 10^4$ |
|  | 70 | $2.23 \times 10^4$ |
| Fluorenone perester (Formula IV) | 10 | $3.15 \times 10^4$ |
|  | 25 | $3.87 \times 10^4$ |
|  | 40 | $4.15 \times 10^4$ |
|  | 70 | $5.0 \times 10^4$ |
| Anthracene perester (Formula V) | 20 | $1.0 \times 10^5$ |
|  | 35 | $1.3 \times 10^5$ |
|  | 70 | $7.9 \times 10^5$ |
| Pyrene ester perester (Formula III) | 35 | $5.86 \times 10^4$ |
|  | 45 | $7.0 \times 10^4$ |
|  | 60 | $7.9 \times 10^4$ |
|  | 100 | $1.58 \times 10^5$ |

TABLE 4

Photopolymerization of Styrene (Bulk) Initiated by Various Peresters

| Initiator | Photopolymerization Time (Hours) | Mn |
|---|---|---|
| Pyrene Ester Perester (Formula III) | 1 | $2.5 \times 10^4$ |
|  | 3.15 | $5.6 \times 10^4$ |
|  | 5 | $6.3 \times 10^4$ |
| Fluorenone Perester (Formula IV) | 3 | $1.17 \times 10^5$ |
|  | 6 | $1.12 \times 10^5$ |
|  | 10.15 | $1.05 \times 10^5$ |
| Pyrene Ketone Perester (Formula II) | 4.20 | $2.5 \times 10^4$ |
|  | 6.15 | $3.1 \times 10^4$ |
|  | 10.30 | $1.4 \times 10^5$ |
| Anthracene Perester (Formula V) | 1.30 | $1.78 \times 10^5$ |
|  | 3 | $2.3 \times 10^5$ |
|  | 4.50 | $2.8 \times 10^5$ |

Figure 10:
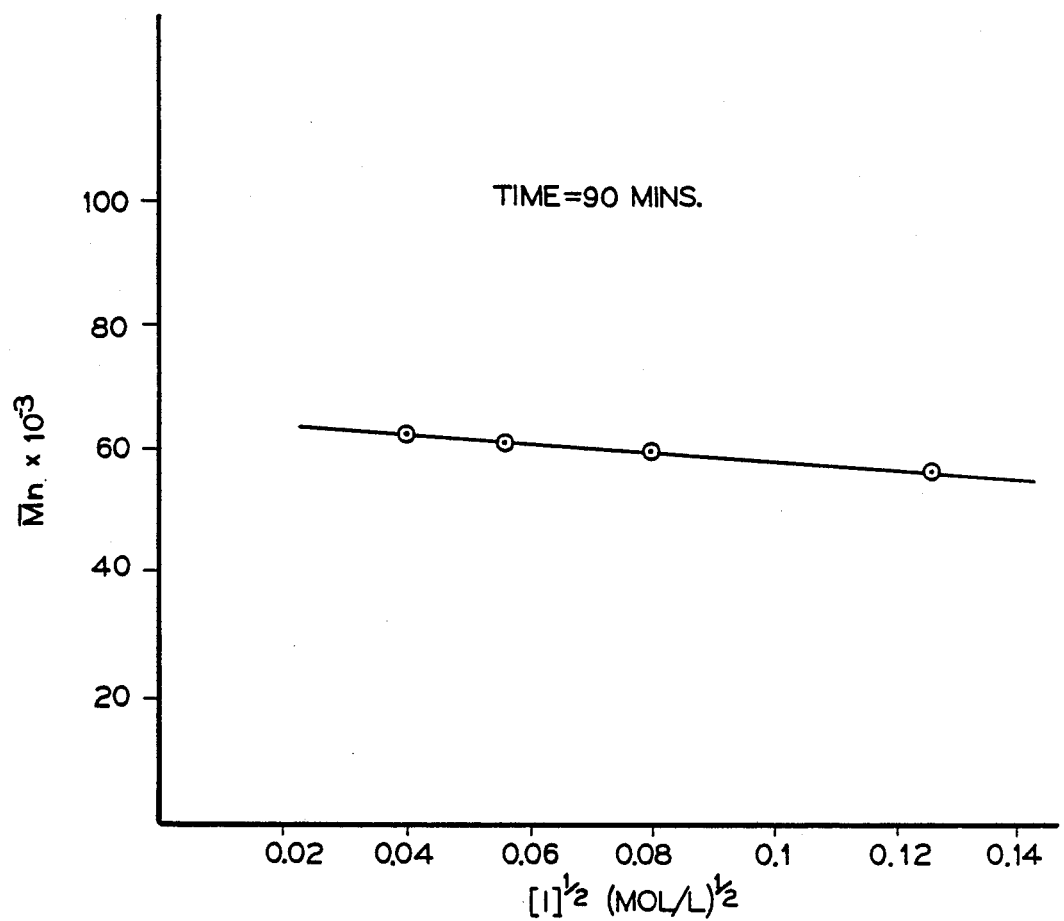
FIG. 10 is a graph showing dependence of the molecular weight of the polymer on the initiator concentration for photopolymerization of MMA (bulk) initiated by pyrene ester perester (Formula III).

FIG. 10 shows that the molecular weight of the MMA formed from one of the aromatic photoinitiators is inversely proportional to the square root of the initiator concentration.

Figure 11:
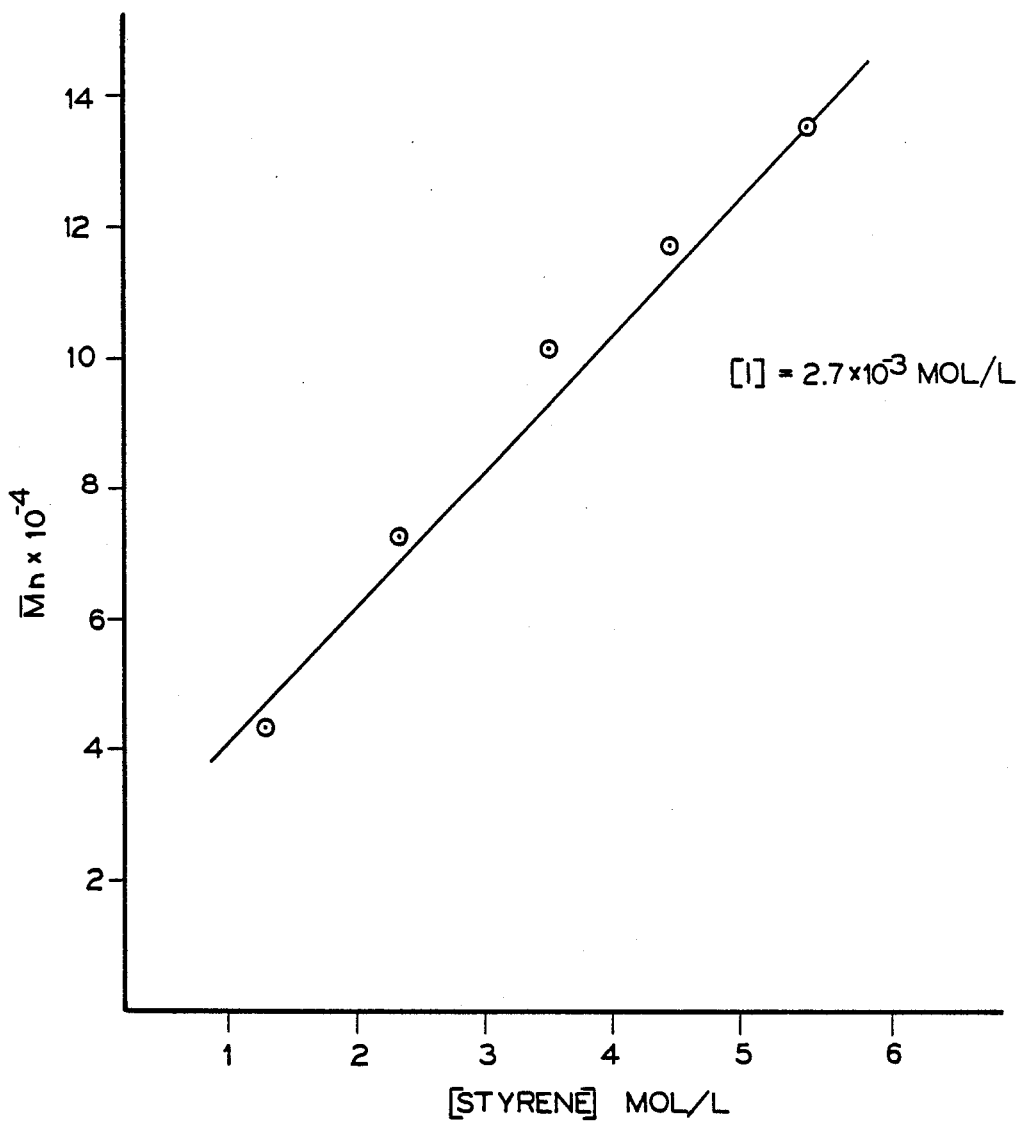
FIG. 11 is a graph showing dependence of the molecular weight of the polymer on the monomer concentration for photopolymerization of styrene initiated by anthracene perester (Formula V).

FIG. 11 shows that the molecular weight of polystyrene formed from the anthracene perester photoinitiation increases as the monomer concentration increases.

Figure 12:
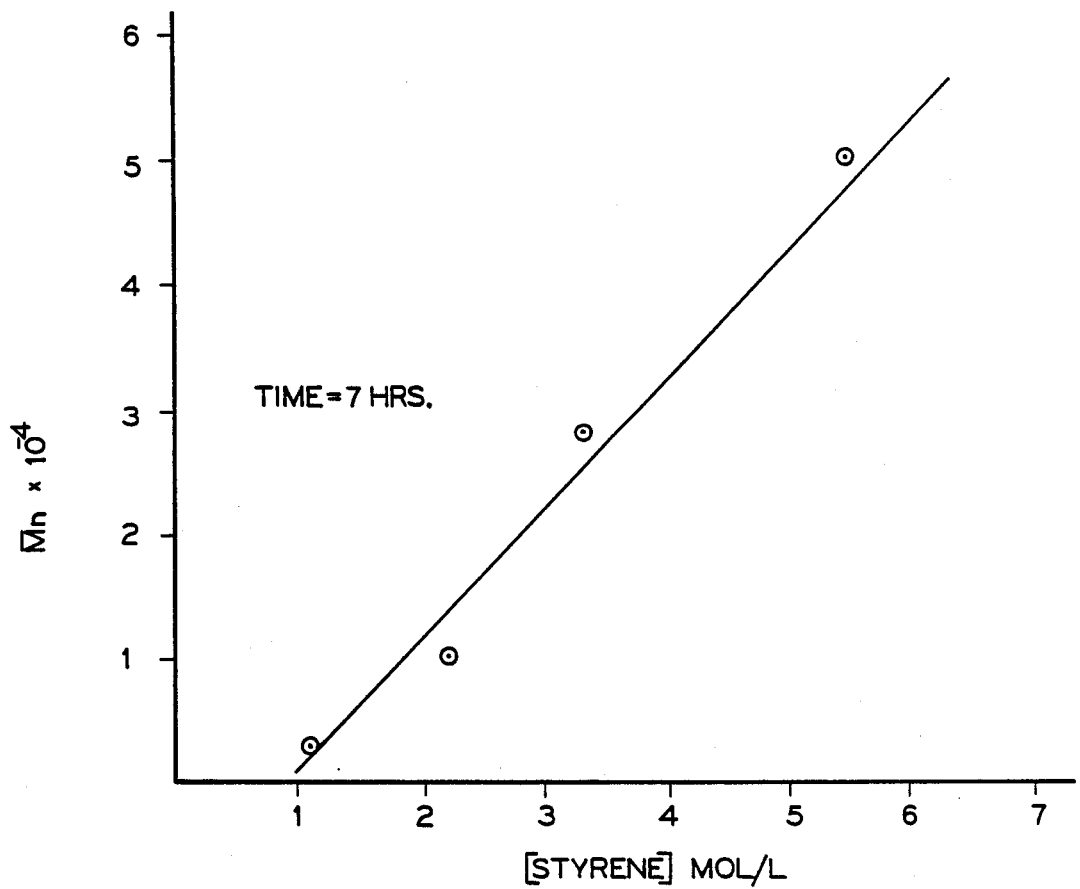
FIG. 12 is a graph showing photopolymerization of styrene bulk initiated by pyrene ester perester (Formula III).

FIG. 12 shows the same relationship between styrene concentration and its polymer molecular weight where the initiator is the pyrene Formula III ester system.

It is an anomoly that though the rate of polymerization of styrene with the Formula V initiator is 1 to 2 orders of magnitude larger than for the Formula III initiator, the Mn of polymers deriving from the Formula V initiator are higher than with the Formula III. The polycyclic aromatic hydrocarbons also serve as radical quenchers. Thus, these peresters also participate in non-initiating reactions with growing radical chains. This is demonstrated by polymerization on the appropriate monomer thermally with AIBN in the presence of the Formula II, III, IV and V initiators. All monomers except Formula IV terminate radical chains sufficiently to decrease the rate of polymerization by as much as 10% when present in concentrations equivalent to those of the AIBN initiator at 70° C.

To test the thermal stability of the perester, attempts are made to measure decomposition rates at 80° C. in benzene. While Bz₂O₂ shows a decomposition rate comparable to the literature value, the peresters do not decompose at all at 80° C. The thermal rates of decomposition in the dark are measured at 110° C. in chlorobenzene and are comparable in value to the rates of decomposition of substituted tert-butyl perbenzoates.

The peresters all provide efficient photochemical sources of free radicals. Important from a practical view is that their photodecomposition is controllable (effectively it can be tuned) by the absorption characteristics of the absorbing chromophore.

The above detailed description of the present invention is given for explanatory purposes. It will be apparent to those skilled in the art that numerous changes and modifications can be made in the preferred embodiments of the invention described above without departing from the scope of the invention. Accordingly, the whole of the foregoing description is to be construed in an illustrative and not in a limitative sense, the scope of the invention being defined solely by the appended claims.

I claim:

1. A compound of formula

R₁—YArCOOOR wherein R is C₁-C₂₂ alkyl; Ar is selected from the group consisting of phenyl, naphthyl, anthryl, pyryl, and phenanthryl; Y is selected from the group consisting of —CH₂—, C═O, and C═N; R₁ is selected from the group of C₁-C₂₂ alkyl, C₃-C₂₂ cycloalkyl, C₆-C₂₂ aryl, and C₇-C₂₂ arylalkyl R₁ absorbing radiation between 250 and 800 nm such that R₁ is a light absorbing chromophore group that produces an excited state by light absorption; except that when Ar is phenyl, Y is not C═O and R₁ is not C₁-C₂₂ alkyl or C₆-C₂₂ aryl.

2. The compound of claim 1 wherein R contains 1-12 carbon atoms.

3. The compound of claim 1 wherein R contains a tertiary carbon atom connected to the oxygen atom.

4. The compound of claim 1 wherein R is tertbutyl.

5. A compound of the formula:

 R₁—YArCOOOR wherein R is C₁-C₂₂ alkyl; Ar is phenyl; Y is selected from the group consisting of —CH₂— and C═N; R₁ is selected from the group of C₁-C₂₂ alkyl, C₃-C₂₂ cycloalkyl, C₆-C₂₂ aryl, and C₇-C₂₂ arylalkyl; R₁ absorbing radiation between 250 and 800 nm such that R₁ is a light absorbing chromophore group that produces an excited state by light absorption.

6. A compound of the formula:

R₁—YArCOOOR wherein R is C₁-C₂₂ alkyl; Ar is phenyl, Y is selected from the group consisting of, —CH₂—, and C═N; R₁ is C₁₀-C₂₂ polycyclic aryl, R₁ absorbing radiation between 250 and 800 nm such that R₁ is a light absorbing chromophore group that produces an excited state by light absorption.

7. The compound of claim 5 wherein R is a tert.butyl.

8. The compound of claim 6 wherein R is a tert.butyl group.

9. The compound of claim 8 wherein Y is C═O.

10. The compound of claim 9 wherein R₁ is pyrenyl.

11. The compound of formula R₁—Y—Ar—COOOR wherein R is a tert.butyl group, Ar is phenyl, Y is C═O and R₁ is pyrenyl, said compound having the structure:

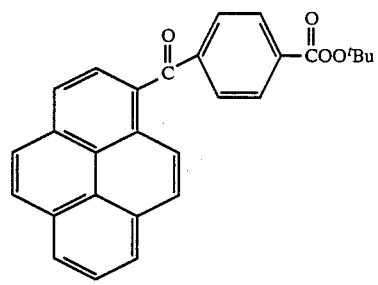

12. The compound of the formula R₁—Y—Ar—COOOR wherein R is a tert.butyl group, Ar is a

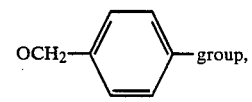 group,

Y is C═O, and R₁ is pyrenyl, said compound having the structure:

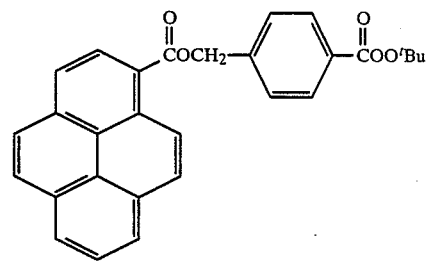

13. The compound of the formula R₁—Y—Ar—COOOR wherein R is a tert.butyl group, Ar is a

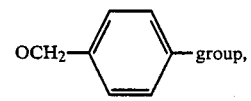 group,

Y is C═O, and R₁ is 9H-fluorenone-9-one-4yl, said compound having the structure:

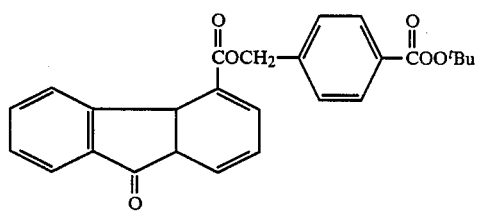

14. The compound of the formula R₁—Y—Ar—COOR wherein R is a tert.butyl group, Ar is a

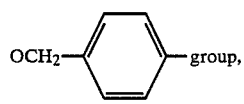 group,
Y is C=O, and $R_1$ is anthryl, said compound having the structure:
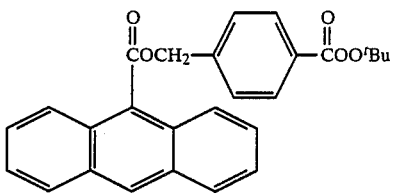
* * * * *